(12) United States Patent
Chen et al.

(10) Patent No.: US 11,335,014 B2
(45) Date of Patent: May 17, 2022

(54) MEDICAL IMAGE DIAGNOSTIC APPARATUS, MEDICAL IMAGE DIAGNOSTIC METHOD, AND ULTRASONIC DIAGNOSTIC APPARATUS

(71) Applicant: CANON MEDICAL SYSTEMS CORPORATION, Otawara (JP)

(72) Inventors: Qi Chen, Beijing (CN); Zhe Tang, Beijing (CN); Weijian Jian, Beijing (CN); Yu Chen, Beijing (CN)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/570,582

(22) Filed: Sep. 13, 2019

(65) Prior Publication Data
US 2020/0090349 A1   Mar. 19, 2020

(30) Foreign Application Priority Data

Sep. 13, 2018 (CN) .......................... 201811066755.6

(51) Int. Cl.
*G06T 7/33* (2017.01)
*G06T 3/40* (2006.01)
*G06T 3/00* (2006.01)
*A61B 8/08* (2006.01)

(52) U.S. Cl.
CPC .............. *G06T 7/33* (2017.01); *A61B 8/0891* (2013.01); *A61B 8/5207* (2013.01); *A61B 8/5261* (2013.01); *G06T 3/0075* (2013.01); *G06T 3/40* (2013.01); *G06T 2207/10132* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 2008/0107312 A1 | 5/2008 | Von Berg | |
| 2008/0221439 A1* | 9/2008 | Iddan | A61B 5/02007 600/424 |
| 2008/0247622 A1* | 10/2008 | Aylward | A61B 90/36 382/131 |
| 2010/0260392 A1 | 10/2010 | Wiemker et al. | |
| 2014/0193053 A1 | 7/2014 | Kadoury et al. | |
| 2015/0055846 A1 | 2/2015 | Haque | |
| 2015/0097833 A1* | 4/2015 | Razeto | G06T 7/30 345/424 |

(Continued)

FOREIGN PATENT DOCUMENTS

| | | |
|---|---|---|
| JP | 2006-217939 A | 8/2006 |
| JP | 2007-524486 A | 8/2007 |

(Continued)

*Primary Examiner* — Jeffrey J Chow
(74) *Attorney, Agent, or Firm* — Oblon, McClelland, Maier & Neustadt, L.L.P.

(57) ABSTRACT

A medical image diagnostic apparatus according to an embodiment includes processing circuitry. The medical image diagnostic apparatus performs image registration between medical image data. The processing circuitry extracts a structure of the subject included in the medical image data. The processing circuitry sets a display scale of the subject to a specified value. The processing circuitry performs image registration between the medical image data on the display scale of the specified value.

13 Claims, 10 Drawing Sheets

(56) References Cited

U.S. PATENT DOCUMENTS

| | | | | |
|---|---|---|---|---|
| 2016/0081658 A1* | 3/2016 | Perrey | ............ | G06T 7/30 |
| | | | | 600/440 |
| 2016/0217576 A1* | 7/2016 | Kabus | ............ | A61B 6/469 |
| 2018/0276820 A1* | 9/2018 | Gibby | ............ | A61B 5/7264 |
| 2018/0330484 A1* | 11/2018 | Bauer | ............ | A61B 6/504 |
| 2020/0046324 A1* | 2/2020 | Veronesi | ............ | A61B 8/5253 |

FOREIGN PATENT DOCUMENTS

| | | |
|---|---|---|
| JP | 2011-506032 A | 3/2011 |
| JP | 2015-39578 A | 3/2015 |

* cited by examiner

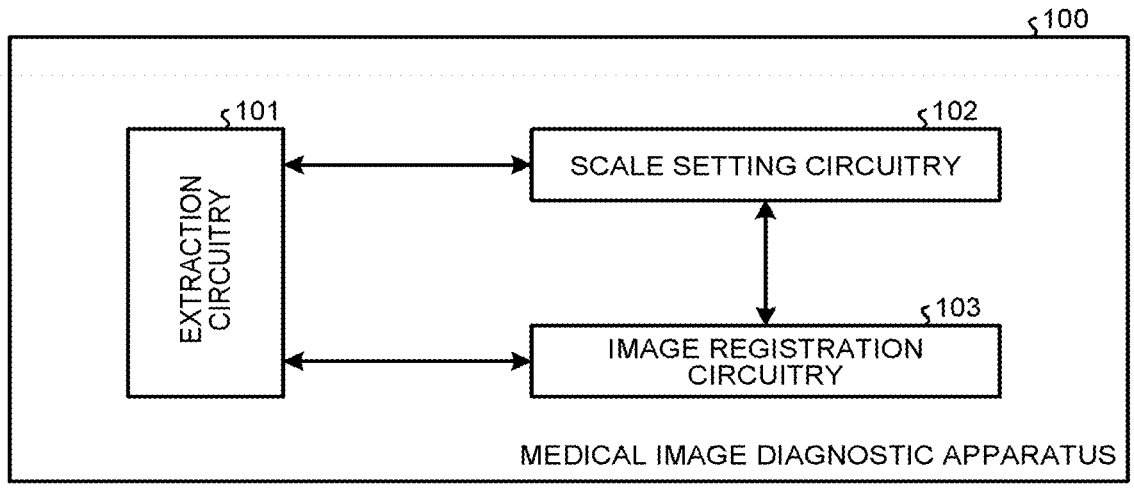
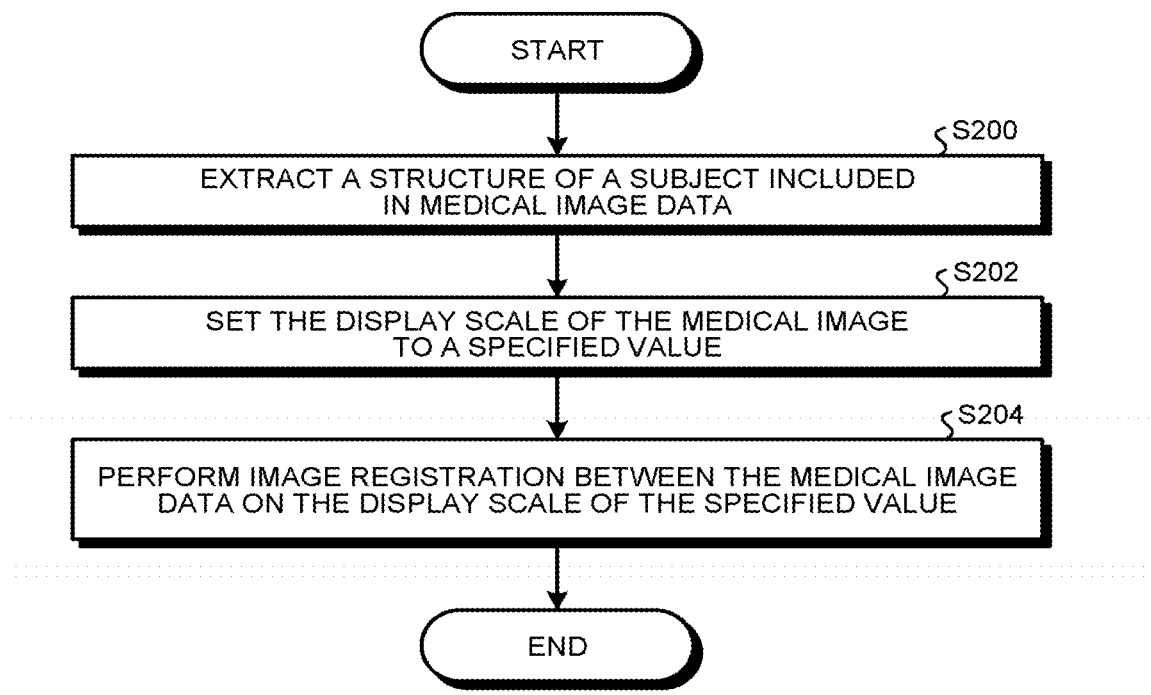

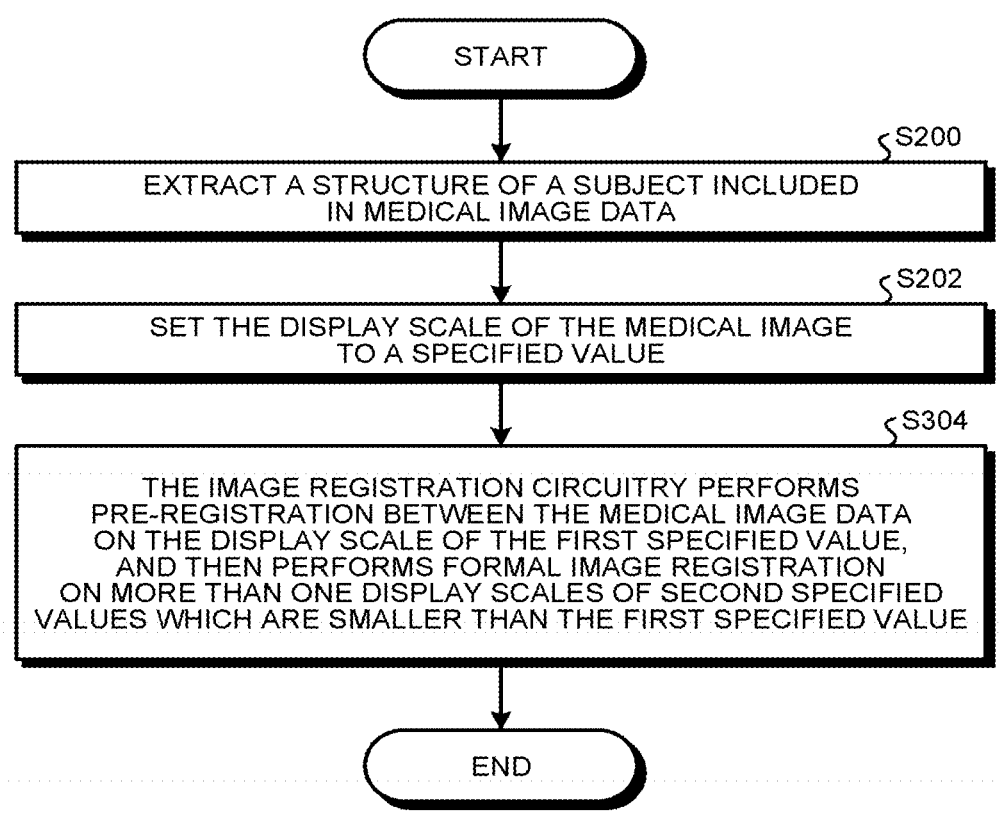

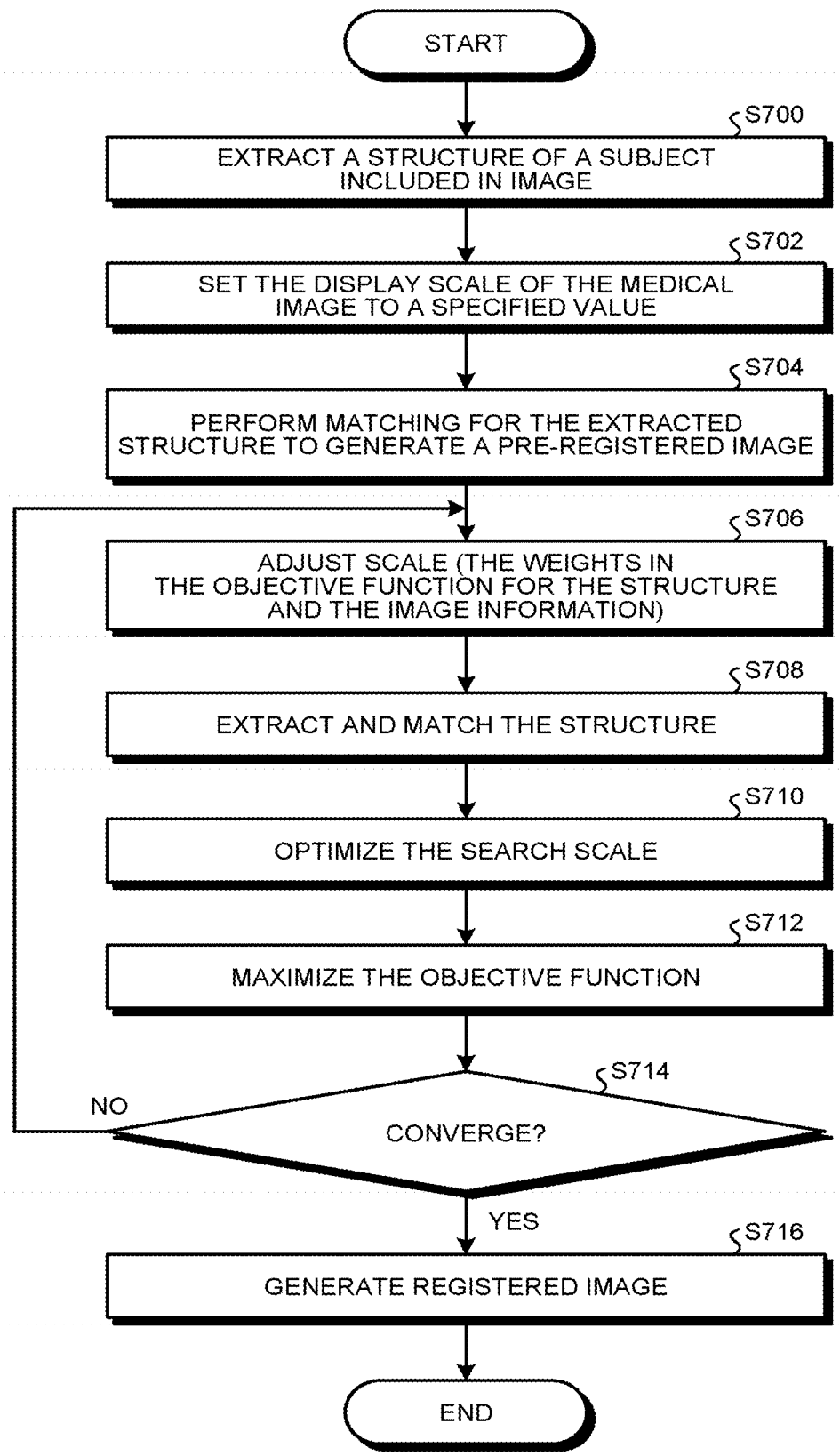

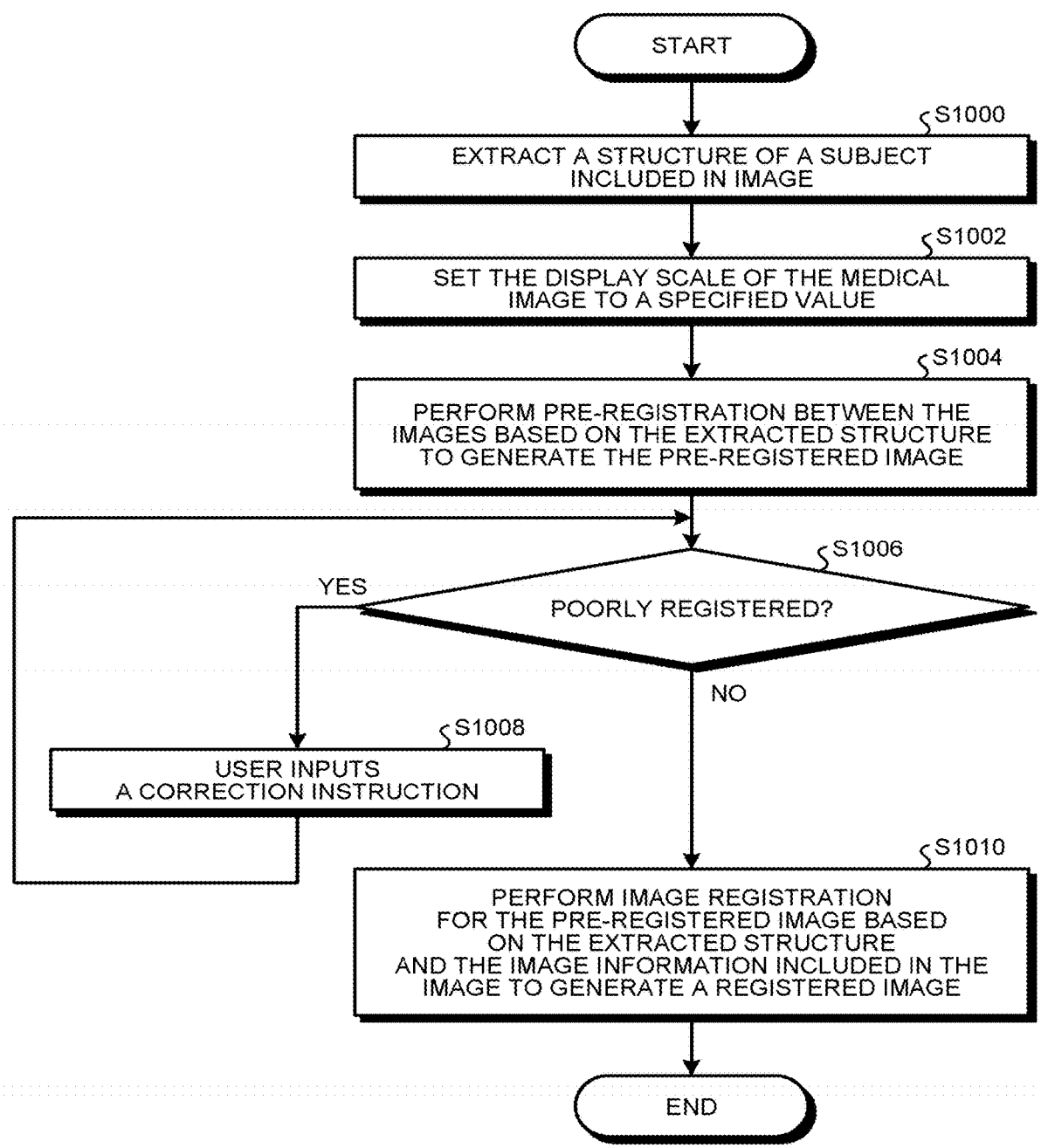

MEDICAL IMAGE DIAGNOSTIC APPARATUS, MEDICAL IMAGE DIAGNOSTIC METHOD, AND ULTRASONIC DIAGNOSTIC APPARATUS

CROSS-REFERENCE TO RELATED APPLICATIONS

This application is based upon and claims the benefit of priority from Chinese Patent Application No. 201811066755.6, filed on Sep. 13, 2018, the entire contents of which are incorporated herein by reference.

FIELD

Embodiments described herein relate generally to a medical image diagnostic apparatus, a medical image diagnostic method and an ultrasonic diagnostic apparatus.

BACKGROUND

At present, the ultrasonic diagnostic apparatus, CT (computed tomography image) imaging apparatus and MR (magnetic resonance) imaging apparatus are widely used in medical related fields. In addition, the ultrasonic diagnostic apparatus has the advantages of no radiation to a subject, good real-time performance and low cost, while the CT imaging apparatus and the MR imaging apparatus, compared with the ultrasonic diagnostic apparatus, can image a higher resolution image, but have poor real-time performance, high cost and radiation to the subject.

Accordingly, it is desirable to combine the advantages of the ultrasound image with those of the CT image/MR image in clinical research and application, as this will help to accurately diagnose and locate lesions of the subject, which is very valuable for the diagnosis and treatment of diseases.

Currently, image registration provides the possibility to implement this technology. Image registration refers to the process of matching and superimposing two or more images acquired at different times, by different sensors (imaging devices) or under different conditions (weather, illumination, camera position and angle, etc.). Presently, it is widely used in the fields such as remote sensing data analysis, computer vision, image processing and so on.

Now, there are researches and applications for registering ultrasound images with CT images/MR images. Generally, at first, the ultrasound images and the CT images/MR images are subjected to preprocessing such as de-noising, up/down sampling, etc., and then the preprocessed images are subjected to feature extraction and points or surfaces in the two parties of the images to be registered, i.e., the ultrasound images and the CT images/MR images are input manually by the user, and then image registration is performed based on the extracted feature according to the points or the surfaces input by the user, and the registered image (also referred to fused image) is displayed. The user can confirm whether the registered image meets the demand. If the demand is met, the diagnosis or treatment for diseases can be performed. If the demand is not met, the user manually inputs points or surfaces again and then performs the registration again until the registered image meets the demand.

However, since the ultrasound image is a two-dimensional image and the CT image is a three-dimensional image, it is very difficult for the user to select an appropriate initial position (for example, a surface) for the registration with the ultrasound image in the three-dimensional CT image.

In addition, after the user manually performs the initial input, the image registration based on the extracted features needs to traverse the entire image, so a serious problem for the registration of such ultrasound images with CT images/MR images is that the registration is very time-consuming.

In addition, the user confirms whether the registration result meets the demand after each registration is completed, and it is needed to re-input points or surfaces when the demand is not met. This way, on the one hand, the user may need to perform a plurality of difficult input operations, on the other hand, the user may need to wait a very time-consuming period for completing the registration process before the user confirms the registration result. Therefore, to obtain the registration result satisfying the demand, the user needs to perform the input multiple times, which takes a long time.

In addition, the accuracy of image registration is highly dependent on the accuracy of feature extraction. If the accuracy of feature extraction is poor, even if the user repeatedly performs the input multiple times, the registration of ultrasound images and CT images/MR images cannot be achieved and thus it is difficult to guarantee the accuracy of the registration.

Therefore, there is an urgent need for a medical image diagnostic apparatus and method that can solve the above problems.

BRIEF DESCRIPTION OF THE DRAWINGS

FIG. 1 is a schematic diagram of the configuration of the medical image diagnostic apparatus according to the first embodiment.

FIG. 2 is an operation flowchart of the medical image diagnostic apparatus according to the first embodiment.

FIG. 3 is an operation flowchart of the medical image diagnostic apparatus according to embodiment 1 of the first embodiment.

FIG. 7 is an operation flowchart of the medical image diagnostic apparatus according to the second embodiment.

FIG. 10 is an operation flowchart of the medical image diagnostic apparatus according to the third embodiment.

DETAILED DESCRIPTION

Figure 4:
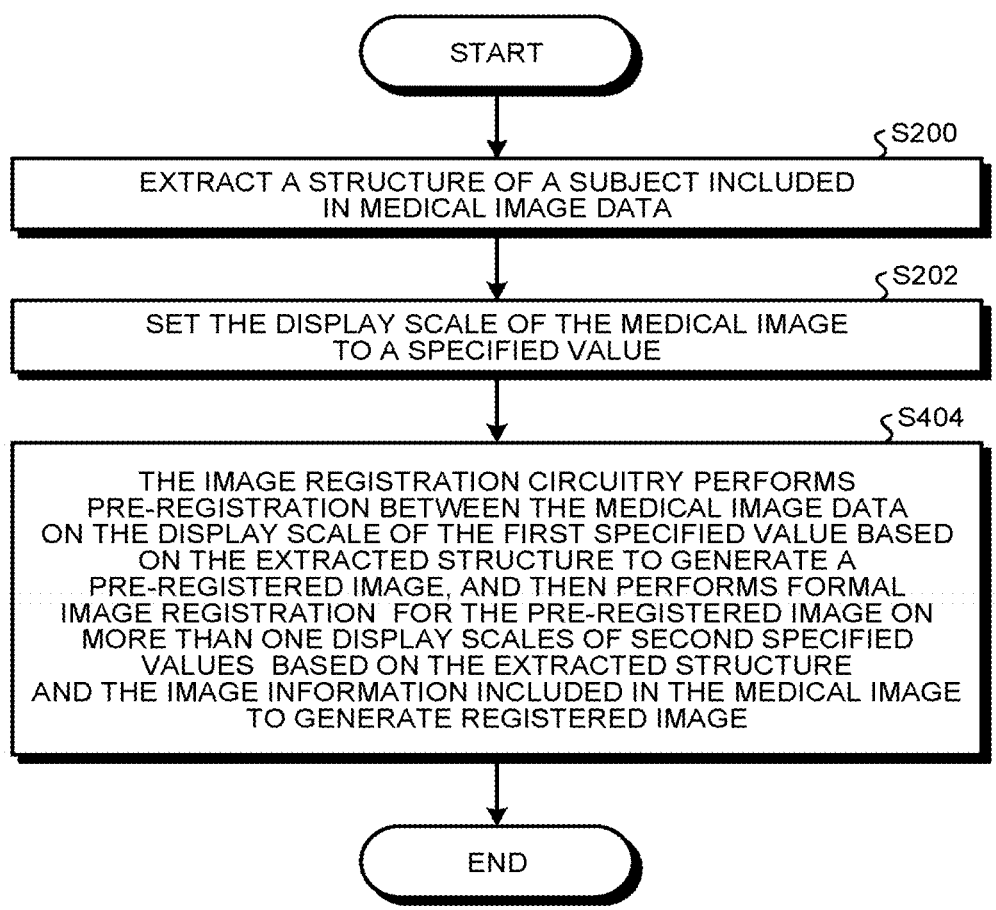
FIG. 4 is an operation flowchart of the medical image diagnostic apparatus according to embodiment 2 of the first embodiment.

The present embodiment provides a medical image diagnostic apparatus for performing image registration between medical image data, characterized by comprising: extraction circuitry for extracting a structure of a subject included in the medical image data; scale setting circuitry for setting a display scale of the medical image to a specified value; and image registration circuitry for performing the image registration between the medical image data on the display scale of the specified value.

Further, the medical image diagnostic apparatus provided by the present embodiment is characterized in that the structure is a blood vessel or a surface contour.

Further, the medical image diagnostic apparatus provided by the present embodiment is characterized in that the image registration circuitry performs pre-registration between the medical image data on the display scale of a first specified value and then performs formal image registration on more than one display scales of second specified values which are smaller than the first specified value.

Further, the medical image diagnostic apparatus provided by the present embodiment is characterized in that the image registration circuitry performs pre-registration between the medical image data on the display scale of the first specified value based on the structure extracted by the extraction circuitry to generate a pre-registered image and performs formal image registration for the pre-registered image on the more than one scales of the second specified values based on the structure extracted by the extraction circuitry and image information included in the medical image to generate a registered image.

Further, the medical image diagnostic apparatus provided by the present embodiment is characterized in that the image information is at least one of the grayscale or gradient of the image.

Further, the medical image diagnostic apparatus provided by the present embodiment is characterized by further comprising: scale adjustment circuitry for adjusting the display scale, wherein the scale adjustment circuitry gradually decreases the specified value set by the scale setting circuitry when the image is registered.

Further, the medical image diagnostic apparatus provided by the present embodiment is characterized by further including input circuitry for inputting a correction instruction by at least an operator, wherein the input circuitry accepts the correction instruction input by the operator if the image registration performed by the image registration circuitry is poor.

Further, the medical image diagnostic apparatus provided by the present embodiment is characterized in that the correction instruction from the input circuitry is rotation and/or translation for one party of the medical image data or point designation in both parties of the medical image data.

Further, the present embodiment provides a medical image diagnostic method for performing image registration between medical image data, characterized by comprising: an extraction step of extracting a structure of a subject included in the medical image data; a scale setting step of setting a display scale of the medical image to a specified value; and an image registration step of performing the image registration between the medical image data on the display scale of the specified value.

Further, a medical image diagnostic apparatus according to an embodiment includes processing circuitry. The medical image diagnostic apparatus performs image registration between medical image data. The processing circuitry extracts a structure of the subject included in the medical image data. The processing circuitry sets a display scale of the subject to a specified value. The processing circuitry performs image registration between the medical image data on the display scale of the specified value.

Further, the present embodiment provides a ultrasound diagnostic apparatus, characterized by comprising the medical image diagnostic apparatus described above.

In the following, the medical image diagnostic apparatus, the medical image diagnostic method and the ultrasound diagnostic apparatus of the embodiments are illustrated with reference to the drawings.

The First Embodiment (The Configuration of the Medical Image Diagnostic Apparatus 100)

At first, the configuration of the medical image diagnostic apparatus 100 according to the first embodiment is illustrated with reference to FIG. 1.

Further, the medical image diagnostic apparatus 100 includes various components, and only the components related to the technical idea of the present embodiment are shown in FIG. 1, and other components are omitted. For example, the medical image diagnostic apparatus may include a display which is composed of, for example, a CRT (Cathode Ray Tube) display, a liquid crystal display, a touch panel or the like and has display function for displaying various images including ultrasonic images, CT images, MR images, pre-registered images and registered images which are the images used for image registration. Also, the display can also inform various kinds of information.

The medical image diagnostic apparatus 100 of the present embodiment performs image registration between the medical image data of the subject. Here, the structure of the subject is usually an affected part, for example, an organ such as a liver, a heart or a lung. The images for the image registration performed by the medical image diagnostic apparatus 100 are two or more images and may be medical images. For example, for the images used for the image registration, one party of the images are ultrasound images, and the other party of the images are CT images (i.e., computed tomography images) or MR images (i.e., magnetic resonance images) and so on.

In addition, the ultrasonic image, the CT image and the MR image which are images for image registration may be acquired in advance by well-known devices and methods and provided to the medical image diagnostic apparatus 100 of the present embodiment. Here, the description of the acquisition of the images for the image registration is omitted.

As shown in FIG. 1, the medical image diagnostic apparatus 100 of the present embodiment includes extraction circuitry 101, scale setting circuitry 102 and image registration circuitry 103.

The extraction circuitry 101 extracts the structure of the subject included in the medical image data for the image registration. Here, the structure may be at least one of a blood vessel or a surface contour. The method of extracting the structure by the extracting circuitry 101 may be, for example, the well-known method of extracting/segmenting the blood vessel contour/center line depending on the structure, or may be the method of extracting/segmenting the surface contour/edge of the organ which is the structure of the subject. Here, the methods described above are not described again. The extraction circuitry 101 is realized by using a processor, for example.

The scale setting circuitry 102 sets the display scale of the medical image to a specified value. Here, the scale setting circuitry 102 may be, for example, a hardware device which can perform an input operation to complete the setting. The hardware device may be, for example, a mouse, a keyboard, a joystick, a trackball, a touch panel, a light pen, a language controller and so on. Alternatively, the scale setting circuitry 102 may be implemented by software by receiving the input of the hardware device. Further, in the present embodiment, the larger the display scale is, the larger the structure is displayed, and the smaller the display scale is, the more the structures are displayed on the screen. Further, in the present embodiment, the larger the display scale of the specified value set by the scale setting circuitry 102, i.e., the larger the structure is displayed, the more the detail information is displayed.

The image registration circuitry 103 performs image registration between the medical image data on the display scale of the specified value. The method of the image registration is, for example, a matching method and so on. The image registration circuitry 103 is realized by using a processor, for example.

Further, the extraction circuitry 101, the scale setting circuitry 102 and the image registration circuitry 103 described above may be different components or modules, but some or all of them may be integrated into one component or module.

Further, the medical image diagnostic apparatus 100 may include a control circuitry that controls the overall operation of the medical image diagnostic apparatus 100, although the control circuitry is not shown in the medical image diagnostic apparatus 100. The extraction circuitry 101, the scale setting circuitry 102 and the image registration circuitry 103 can cooperate to complete the image registration function under the control of the control circuitry. The control circuitry is realized by using a processor, for example.

(The Operation of the Medical Image Diagnostic Apparatus 100)

In the following, the medical image diagnostic apparatus 100 according to the first embodiment and the medical image diagnostic method applied thereto will be illustrated based on an operation flowchart.

FIG. 2 is an operation flowchart of the medical image diagnostic apparatus 100 according to the first embodiment.

As shown in FIG. 2, in the step S200, the medical image diagnostic apparatus 100 extracts the structure of the subject included in the medical image data for image registration by the extraction circuitry 101, and then the operation process proceeds to step S202.

In step S202, the medical image diagnostic apparatus 100 sets the display scale of the medical image to a specified value by the scale setting circuitry 102, and then the operation process proceeds to step S204. Here, the display scale is set to be relatively large.

In step S204, the medical image diagnostic apparatus 100 performs image registration between the medical image data on the display scale of the specified value by the image registration circuitry 103, and then the operation process ends.

According to the medical image diagnostic apparatus 100 of the first embodiment, the extraction circuitry 101 extracts a relatively microscopic structure from the image, sets the display scale to be relatively large, and performs registration through, for example, matching method using the relatively microscopic structure. As such, the time of the registration processing can be shortened, the image quality requirement of the acquired image can be reduced, the dependence on the feature extraction can be reduced, and the situation where image registration cannot be achieved can be largely avoided. Also, the structure can be extracted more easily and accurately on a large display scale, which is advantage for achieving high registration accuracy.

Embodiment 1

In the following, the medical image diagnostic apparatus 100 according to embodiment 1 of the first embodiment will be illustrated.

(The Configuration of the Medical Image Diagnostic Apparatus 100 According to Embodiment 1)

The configuration of the medical image diagnostic apparatus 100 according to embodiment 1 is shown in FIG. 1, and the description thereof is omitted here.

Further, in embodiment 1, the image registration circuitry 103 performs pre-registration between the medical image data on the display scale of the first specified value (sometimes referred to the first display scale), and then performs formal image registration on more than one display scales of second specified values (sometimes referred to the second display scale) which are smaller than the first specified value.

In addition, the first display scale and the second display scale here may be, for example, the scale when the extraction circuitry 101 extracts the structure in the image.

(The Operation of the Medical Image Diagnostic Apparatus 100 According to Embodiment 1)

FIG. 3 is an operational flowchart of the medical image diagnostic apparatus 100 according to embodiment 1 of the first embodiment.

As shown in FIG. 3, in the step S200, the medical image diagnostic apparatus 100 extracts the structure of the subject included in the medical image data for image registration by the extraction circuitry 101, and then the operation process proceeds to step S202.

In step S202, the medical image diagnostic apparatus 100 sets the display scale of the medical image to a specified value by the scale setting circuitry 102, and then the operation process proceeds to step S304. Here, the display scale is set to be relatively large.

In step S304, the medical image diagnostic apparatus 100 performs pre-registration between the medical image data on the display scale of the first specified value by the image registration circuitry 103, and then performs formal image registration on more than one display scales of the second specified values which are smaller than the first specified value, and then the operation process ends.

The medical image diagnostic apparatus 100 according to embodiment 1 of the first embodiment has the technical effect of the first embodiment. Moreover, the image registration circuitry 103 performs pre-registration between the medical image data on the display scale of the first specified value, and then performs formal image registration on more than one display scales of second specified values which are smaller than the first specified value, that is, performs approximate, partial registration for the image through for example matching method using the relative microscopic structure, and then performs finer registration on the display scales of the second specified values which are smaller than the first specified value under the consideration of the relative macroscopic image information in the image, thereby achieving fine and global image registration. Thus, the combination of the local registration with the global registration enables an automatic registration from coarse registration to fine registration.

Embodiment 2

In the following, the medical image diagnostic apparatus 100 according to embodiment 2 of the first embodiment will be illustrated.

(The Configuration of the Medical Image Diagnostic Apparatus 100 According to Embodiment 2)

The configuration of the medical image diagnostic apparatus 100 according to embodiment 2 is shown in FIG. 1, and the description thereof is omitted here.

Further, in the embodiment 2, the image registration circuitry 103 performs pre-registration between the medical image data on the display scale of the first specified value based on the structure extracted by the extraction circuitry 101 to generate a pre-registered image, and performs formal image registration for the pre-registered image on more than one display scales of the second specified values based on the structure extracted by the extraction circuitry 101 and the image information included in the medical image to generate a registered image.

(The Operation of the Medical Image Diagnostic Apparatus 100 According to Embodiment 2)

FIG. 4 is an operation flowchart of the medical image diagnostic apparatus 100 according to embodiment 2 of the first embodiment.

As shown in FIG. 4, in the step S200, the medical image diagnostic apparatus 100 extracts the structure of the subject included in the medical image data for image registration by the extraction circuitry 101, and then the operation process proceeds to step S202.

In step S202, the medical image diagnostic apparatus 100 sets the display scale of the medical image to a specified value by the scale setting circuitry 102, and then the operation process proceeds to step S404. Here, the display scale is set to be relatively large.

In step S404, the medical image diagnostic apparatus 100 performs pre-registration between the medical image data on the display scale of the first specified value by the image registration circuitry 103 based on the structure extracted by the extraction circuitry 101 to generate a pre-registered image, and performs formal image registration for the pre-registered image on more than one display scales of the second specified values based on the structure extracted by the extraction circuitry 101 and the image information included in the medical image to generate a registered image. Then the operation process ends.

In the following, the medical image diagnostic apparatus 100 according to embodiment 2 of the first embodiment will be illustrated by way of specific examples.

Figure 5A:
FIGS. 5A to 5G are schematic diagrams of display examples of the medical image diagnostic apparatus according to embodiment 2 of the first embodiment.
Figure 5B:

In embodiment 2 of the first embodiment, the ultrasound image for the liver which is the structure of the subject shown in FIG. 5A and the CT image for the liver which is the same structure of the same subject shown in FIG. 5B are registered.

Figure 5C:
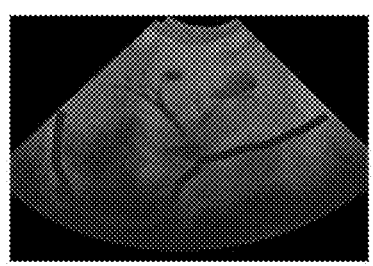
Figure 5D:
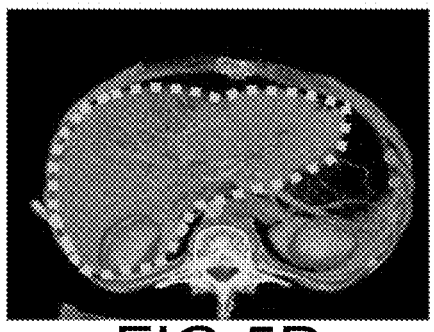

First, the medical image diagnostic apparatus 100 extracts the structure of the subject (for example, the surface contour of the liver of the subject here) included in the medical image data for image registration by the extraction circuitry 101 (Step S20). For example, a curve shown by a solid line in FIG. 5C is extracted from the ultrasonic image, and a curve shown by a dash line in FIG. 5D is extracted from the CT image.

Next, the medical image diagnostic apparatus 100 sets the display scale of the medical image to a specified value by the scale setting circuitry 102 (Step S202). Here, for example, the display scale is the first display scale.

Then, the medical image diagnostic apparatus 100 performs pre-registration between the medical image data on the first display scale through the method such as image matching and so on by the image registration circuitry 103 based on the structure extracted by the extraction circuitry 101 (the curve shown by the solid line in FIG. 5C and the curve shown by the dash line in FIG. 5D) to generate a pre-registered image. Then, the medical image diagnostic apparatus 100 performs formal image registration for the pre-registered image on the second display scales which are smaller than the first display scale by the image registration circuitry 103 based on the structure extracted by the extraction circuitry 101 and the image information such as the grayscale or gradient and so on included in the image to generate a registered image (Step S404).

Figure 5E:
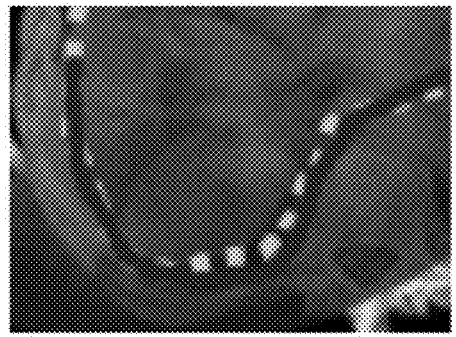
Figure 5F:
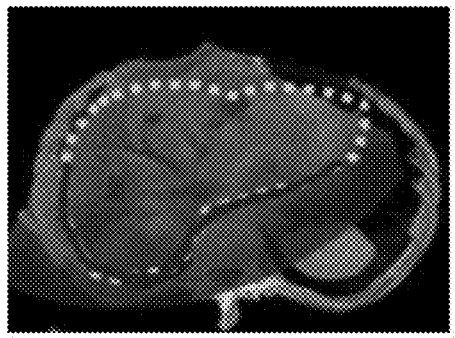
Figure 5G:
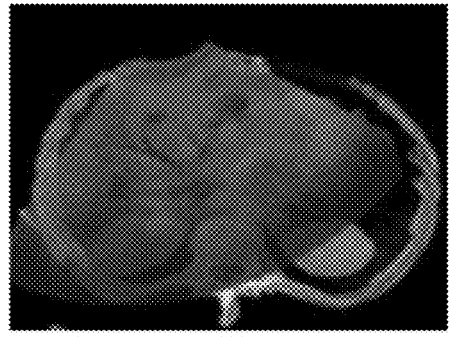

Here, the pre-registered image is generated by means of superposing the ultrasound image (i.e., the partial curve shown by a solid line in FIG. 5C) and the CT image (i.e., the partial curve shown by a dash line in FIG. 5D) in a roughly overlapping way, as shown in FIG. 5E. In addition, the registered image may be generated by means of superposing the ultrasound image (i.e., the curve shown by a solid line in FIG. 5C) and the CT image (i.e., the curve shown by a dash line in FIG. 5D) in an overlapping way better than that in the pre-registered image shown in FIG. 5E, as shown in FIG. 5F. Further, the registered image may be displayed after the ultrasound image and the CT image are registered, but may not clearly represent the matching situation of the structure, as shown in FIG. 5G. Then, the operation process ends.

The medical image diagnostic apparatus 100 according to embodiment 2 of the first embodiment also has the technical effect of the first embodiment described above. Further, the extraction circuitry 101 extracts a relatively microscopic structure from the image and uses the relatively microscopic structure to perform approximate, local registration between the medical image data through for example the matching method, and then performs finer registration for the locally registered pre-registered image on the consideration of some relative macroscopic image information such as the grayscale and gradient and so on included in the medical image data in addition to the structure extracted by the extraction circuitry 101, thereby achieving fine and global formal image registration. In this way, at first, appreciate and local registration for image is performed by using the information of the relatively microscopic structure, and then finer registration for the locally registered pre-registered image based on the relatively microscopic structure and the relatively macroscopic image information such as the grayscale and gradient and so on included in the image. As such, the combination of the local registration and the global registration enables an automatic registration from coarse registration to fine registration. Moreover, in the local pre-registration, since only the relatively microscopic and local information is used, the time of the registration processing can be shortened, the image quality requirement for the acquired image can be reduced, the dependence on the feature extraction can be reduced, the situation where the image registration cannot be achieved can be largely avoided. Further, the registration image generating circuitry 103 further performs finer registration for the locally registered pre-registered images based on the relatively microscopic structures and the relatively macroscopic image information included in the images, thereby ensuring high accuracy of the image registration and enabling fine global image registration. In addition, the image registration circuitry 103 performs pre-registration between the medical image data on the first display scale, and further performs formal image registration on more than one second display scales which are smaller than the first display scale, thereby effectively enabling to both shorten the time spent on the image registration and complete fine global registration.

The Second Embodiment

In the following, the medical image diagnostic apparatus 100A according to the second embodiment is illustrated.

(The Configuration of the Medical Image Diagnostic Apparatus 100A)

Figure 6:
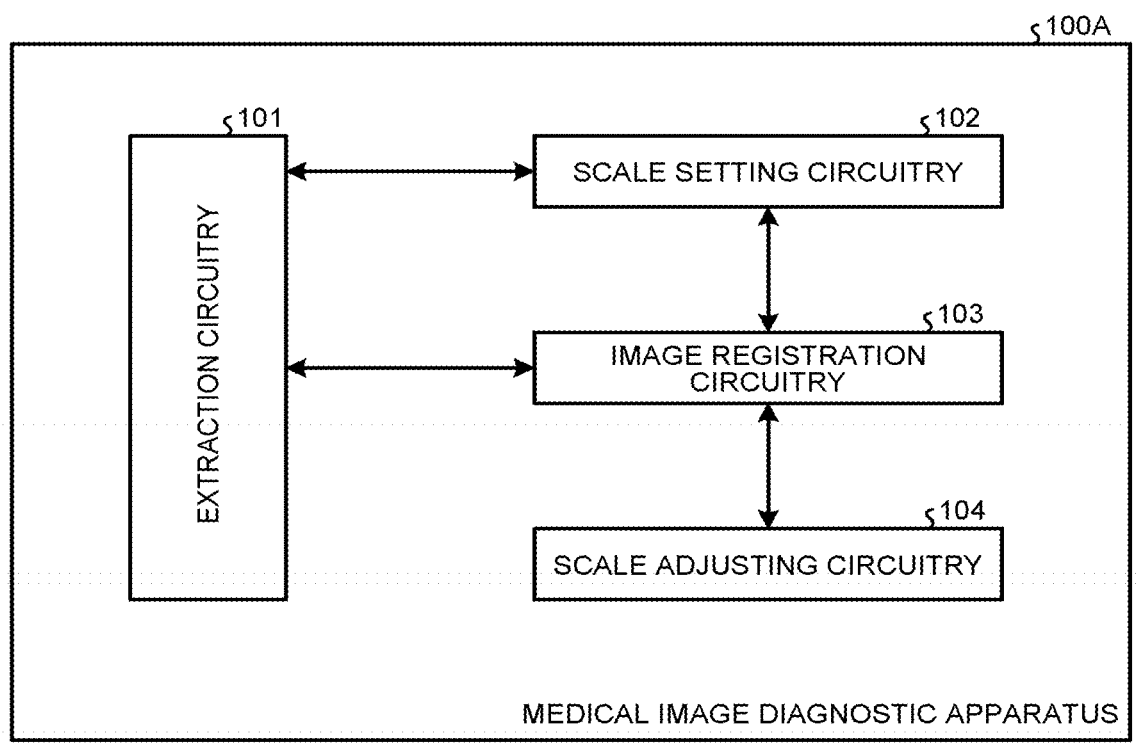
FIG. 6 is a schematic diagram of the configuration of the medical image diagnostic apparatus according to the second embodiment.

FIG. 6 is a schematic diagram of the configuration of the medical image diagnostic apparatus 100A according to the second embodiment. In FIG. 6, the same members as those in FIG. 1 (i.e., the schematic view of the configuration of the medical image diagnostic apparatus 100 according to the first embodiment) are denoted by the same reference numerals, and the description thereof will be omitted.

The medical image diagnostic apparatus 100A according to the second embodiment is different from the medical image diagnostic apparatus 100 according to the first embodiment in that the medical image diagnostic apparatus 100B according to the second embodiment includes scale adjustment circuitry 104. The scale adjustment circuitry 104 adjusts the display scale of the medical image. The mode in which the scale adjustment circuitry 104 adjusts the display scale of the image may be that the display scale is changed in equal amplitude at a specified time interval in a pre-specified manner. Of course, the display scale of the image may also be adjusted by accepting a manual operation by the user. Further, the timing at which the scale adjustment circuitry 104 adjusts the display scale of the image may be in the process of the image pre-registration performed by the image registration circuitry 103, or after the pre-registration and before the formal image registration, or in the process of the formal image registration. The scale adjustment circuitry 104 is realized by using a processor, for example.

Also, in the embodiment, when the image registration circuitry 103 performs the formal image registration, the scale adjustment circuitry gradually decreases the display scale.

(The Operation of the Medical Image Diagnostic Apparatus 100A)

FIG. 7 is an operation flowchart of the medical image diagnostic apparatus 100A according to the second embodiment. In the operation flowchart shown in FIG. 7, step S704 relates to pre-registration, and steps S706 to S716 are implementation procedures of one specific example involving formal image registration.

As shown in FIG. 7, in step S700, the medical image diagnostic apparatus 100A extracts the structure of the subject included in the medical image data for image registration by the extraction circuitry 101, and then the operation process proceeds to step S702.

In step S702, the medical image diagnostic apparatus 100A sets the display scale of the medical image to a specified value by the scale setting circuitry 102, and then the operation process proceeds to step S704. For example, the display scale is the display scale of the first specified value.

In step S704, the medical image diagnostic apparatus 100A performs pre-registration between the medical image data on the first display scale through the methods such as image matching and so on by the image registration circuitry 103 based on the structure extracted by the extraction circuitry 101 to generate a pre-registered image, and then the operation process proceeds to step S706.

In step 706, the medical image diagnostic apparatus 100A adjusts the display scale as the second display scale which is smaller than the first display scale by the scale adjustment circuitry 104. Further, the weights in the objective function for the structure and the image information can be adjusted by a component (not shown) as needed here, and then the operation process proceeds to step S708.

In step S708, the medical image diagnostic apparatus 100A extracts the structure of the subject included in the medical image data for image registration on the second display scale which is smaller than the first display scale by the extraction circuitry 101, and performs a further matching for the structure in the pre-registered image on the second display scale by the image registration circuitry 103 based on the structure extracted by the extraction circuitry 101, and then the operation process proceeds to step S710.

In step S710, the image registration circuitry 103 of the medical image diagnostic apparatus 100A optimizes the scale, and then the operation process proceeds to step S712. In step S712, the image registration circuitry 103 of the medical image diagnostic apparatus 100A maximizes the objective function, and then the operation process proceeds to step S714.

In step S714, the medical image diagnostic apparatus 100A determines whether the objective function converges. If the objective function is determined to not converge (NO in step S714), the operation process returns to step S706 and performs steps S706 to S714 repeatedly (iteratively) until the objective function converges; on the other hand, if the objective function is determined to converge (YES in step S714), the operation process proceeds to step S716.

In step S716, the medical image diagnostic apparatus 100A completes the formal image registration to generate registered image by the image registration circuitry 103 at the time when the objective function converges, and then the operation process ends.

In the following, the medical image diagnostic apparatus 100A of the embodiment will be illustrated by way of specific examples.

Figure 8A:
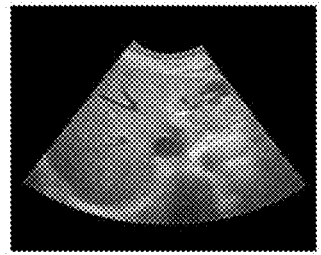
FIGS. 8A to 8H are schematic diagrams of display examples of the medical image diagnostic apparatus according to the second embodiment.
Figure 8B:
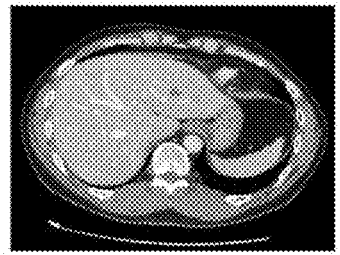

In the embodiment, the ultrasound image of the liver which is the structure of the subject shown in FIG. 8A and the CT image of the liver which is the same structure of the same subject shown in FIG. 8B are registered.

Figure 8C:
Figure 8D:
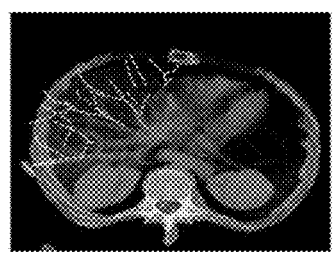

At first, the medical image diagnostic apparatus 100A extracts the structure of the subject (for example, the blood vessel of the liver of the subject here) included in the medical image data for image registration by the extraction circuitry 101 (step S700). For example, the blood vessel of the subject in point and line shape shown by a solid line in FIG. 8C is extracted from the ultrasonic image, and the blood vessel of the subject in line shape shown by a dash line in FIG. 8D is extracted from the CT image.

Then, the medical image diagnostic apparatus 100A sets the display scale of the medical image to a specified value by the scale setting circuitry 102 (step S702), here the display scale is the first specified value.

Figure 8E:

Then, the medical image diagnostic apparatus 100A performs pre-registration between the medical image data on the first display scale through the methods such as image matching (e.g., vessel tree matching, and the display scale is the first display scale of σ1=3 mm and the weight of the vessel tree distance is the weight of ωv=1) by the image registration circuitry 103 based on the structure (the curve shown by a solid line in FIG. 8C and the curve shown by a dash line in FIG. 8D) extracted by the extraction circuitry 101 to generate a pre-registered image (step S704). The pre-registered image is generated by superposing the ultrasound image (i.e., the partial curve shown by a solid line in FIG. 8C) and the CT image (i.e., the partial curve shown by a dash line in the 8D) in a roughly overlapping manner, as shown in FIG. 8E.

Figure 8F:
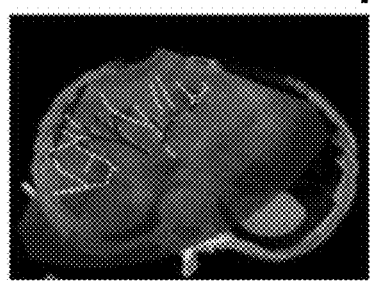
Figure 8G:
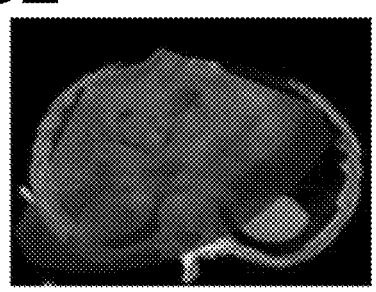
Figure 8H:
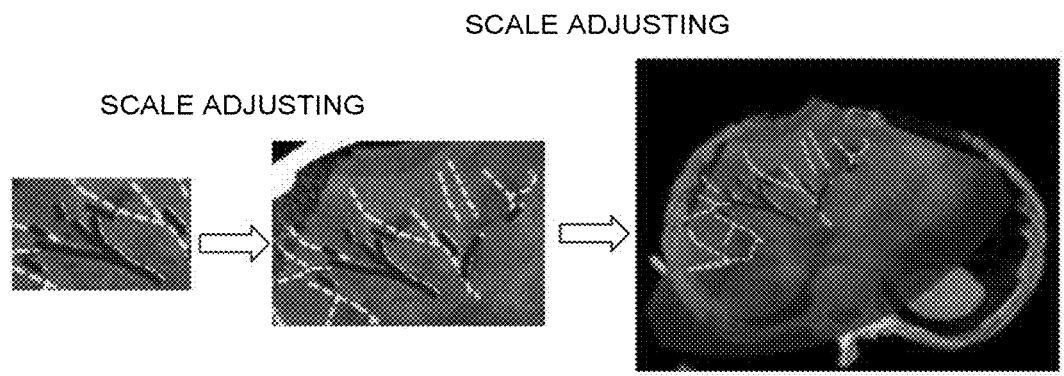

Then, the medical image diagnostic apparatus 100A adjusts the display scale as the second display scale which is smaller than the first display scale by the scale adjustment circuitry 104, as shown in FIG. 8H, i.e., the display scale is adjusted from the first display scale of σ1 on the left side view (i.e., FIG. 8E) to the second display scale of σ2 on the middle view (for example, σ2=2 mm).

Moreover, here, the objective function used in the formal image registration is given by Equation (1):

$$\omega g * Sg - \omega v * Sv \quad (1)$$

wherein, Sg: the global similarity, as presented by Equation (2) for example;

$$S(I_1, I_2) = \frac{1}{|\Omega|} \int_\Omega \langle \overrightarrow{G(I_1(x))}, \overrightarrow{G(I_2(x))} \rangle d\Omega + \frac{1}{|\Omega|} |\Phi|_{I_1(x) \in I_e, I_2(x) \in I_e} \quad (2)$$

The parameters in Equation (2) are given by Equation (3) as follows:

$$\overrightarrow{G(I_1(x))} = \frac{\overrightarrow{f(x)}}{\|f(x)\|}, f(i) = \frac{1}{|P|} \sum_{j \in p} \frac{1}{\|\vec{i} - \vec{j}\|} (I(i) - I(j)) * (\vec{i} - \vec{j}) \quad (3)$$

ωg: the weight of the global similarity;

Sv: the distance of the vessel tree in the pre-registered image used in the image registration performed by the image registration circuitry 103;

ωv: the weight of the distance of the vessel tree.

Here, while the display scale is adjusted from σ1 to σ2, the weight of the distance of the vessel tree is also reduced, for example, ωv=0.75, and the weight of the global similarity ωg is increased, so that ωg=2 (the initial value of ωg is 1) (Step S706).

Then, the medical image diagnostic apparatus 100A extracts the structure (blood vessel) of the subject included in the medical image data for image registration on the second display scale σ2 which is smaller than the first display scale σ1 by the extraction circuitry 101, and performs a further matching for the structure (vessel tree) in the pre-registered image on the second display scale based on the structure extracted by the extraction circuitry 101, here, as shown in the middle view of FIG. 8H, due to the adjustment of the display scale and related parameters, the vessel tree is growing up, and compared with the left side view of FIG. 8H, more data on the smaller scale is added, so that the formal image registration is further refined (step S708).

Then, the scale is optimized (step S710), here, the optimization method may be any well-known optimization method, and the description thereto is omitted here.

Then, the objective function is maximized (step S712).

Then, the medical image diagnostic apparatus 100A determines whether the objective function converges by the image registration circuitry 103. Here, the objective function does not converge (NO in step S714), so the operation process returns to step S706 and performs steps S706 to S714 repeatedly (iteratively). Specifically, for example, the medical image diagnostic apparatus 100A may adjust the display scale to the third display scale by the scale adjustment circuitry 104, as shown in FIG. 8H, i.e., the display scale is adjusted from the second display scale σ2 in the middle view to the third display scale σ3 in the right side view (for example, σ3=1 mm). At the same time, the weight of the distance of the vessel tree is reduced, for example, ωv=0.5, and the weight of the global similarity ωg is increased, so that ωg=3 (step S706).

Then, the iterative process is performed (steps S706 to S712), and the objective function is determined to converge in this iteration (YES in step S714).

Thus, the medical image diagnostic apparatus 100A completes the formal image registration by the image registration circuitry 103 to generate a registered image, which may be generated by superposing the ultrasound image (i.e., the curve shown by a solid line in FIG. 8C) and the CT image (i.e., the curve shown by a dash line in FIG. 8D) in an overlapping way better than that in the pre-registered image shown in FIG. 8E, as shown in FIG. 8F. Further, the registered image may be displayed after the ultrasonic image and the CT image are registered, but may not clearly represent the matching situation of the structure, as shown in FIG. 8G, and then the operation process ends.

The medical image diagnostic apparatus 100A according to the second embodiment has the technical effects of the first embodiment and its respective embodiments, which will not be described repeatedly.

The Third Embodiment

In the following, the medical image diagnostic apparatus 100B according to the third embodiment will be illustrated.
(The Configuration of the Medical Image Diagnostic Apparatus 100B)

Figure 9:
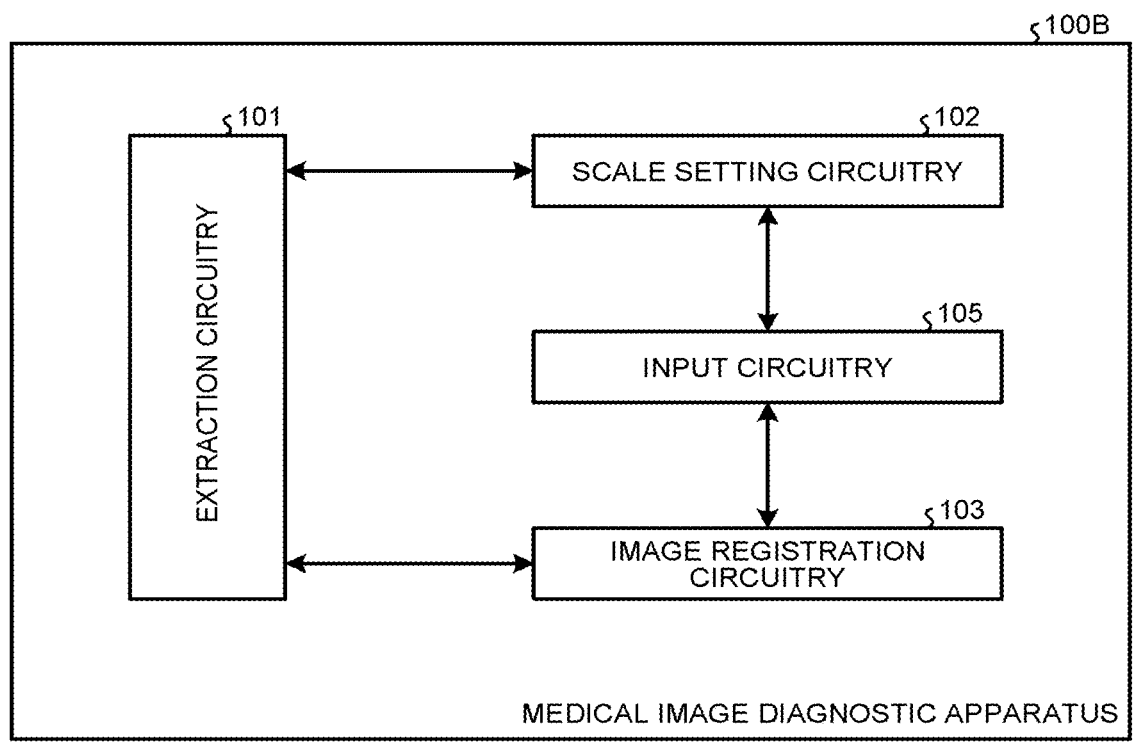
FIG. 9 is a schematic diagram of the configuration of the medical image diagnostic apparatus according to the third embodiment.

FIG. 9 is a schematic diagram of the configuration of the medical image diagnostic apparatus 100B according to the third embodiment. In FIG. 9, the same members as those in FIG. 1 (i.e., the schematic views of the configuration of the medical image diagnostic apparatus 100 according to the first embodiment) are denoted by the same reference numerals, and the description thereto will be omitted.

The medical image diagnostic apparatus 100B according to the third embodiment is different from the medical image diagnostic apparatus 100 according to the first embodiment in that the medical image diagnostic apparatus 100B according to the third embodiment includes input circuitry 106.

The input circuitry 106 is an input interface which is used for inputting a correction instruction by the user, and the input circuitry 106 may be the device which can perform the input, such as a mouse, a keyboard, a joystick, a trackball, a touch screen, a light pen, a language controller and so on.

Further, in the embodiment, when the pre-registered image is poorly registered, the user inputs a correction instruction via the input circuitry 106. Here, the correction instruction is rotation and/or translation for one party of the medical image data or point designation in both parties of the medical image data.
(The Operation of the Medical Image Diagnostic Apparatus 100B)

FIG. 10 is an operation flowchart of the medical image diagnostic apparatus 100B according to the third embodiment.

As shown in FIG. 10, in step S1000, the medical image diagnostic apparatus 100B extracts the structure of the subject included in the medical image data for image registration by the extraction circuitry 101, and then the operation process proceeds to step S1002.

In step S1002, the medical image diagnostic apparatus 100B sets the display scale of the medical image to a specified value by the scale setting circuitry 102, and then the operation process proceeds to step S1004. Here, the display scale is for example the first display scale.

In step S1004, the medical image diagnostic apparatus 100B performs pre-registration between the medical image data on the first display scale through the methods such as image matching by the image registration circuitry 103 based on the structure extracted by the extraction circuitry 101 to generate a pre-registered image, and then the operation process proceeds to step S1006.

In step S1006, the user determines whether the pre-registered image is poorly pre-registered based on the displayed pre-registered image, and if the pre-registered image is determined as being poorly pre-registered (YES in step S1006), the process proceeds to step S1008. In step S1008, the user inputs a correction instruction via the input circuitry 106 and performs step S1006 again. On the other hand, if the pre-registered image is not determined as being poorly pre-registered (NO in step S1006), the process proceeds to step S1010.

In step S1010, the medical image diagnostic apparatus 100B performs formal image registration for the pre-registered image by the image registration circuitry 103 based on the structure extracted by the extraction circuitry 101 and the image information such as the gradation or gradient and so on included in the image to generate a registered image. Then, the operation process ends.

In the following, a medical image diagnostic apparatus 100B of the embodiment will be illustrated by way of specific examples.

Figure 11A:
FIGS. 11A to 11G are schematic diagrams of display examples of the medical image diagnostic apparatus according to the third embodiment.
Figure 11B:
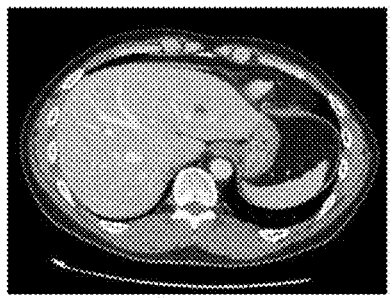

In the embodiment, the ultrasound image of the liver which is the structure of the subject shown in FIG. 11A and the CT image of the liver which is the same structure of the same subject shown in FIG. 11B are registered.

Figure 11C:
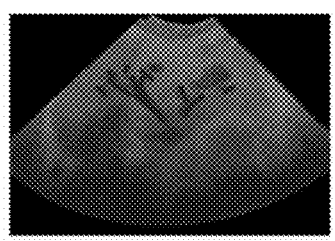
Figure 11D:
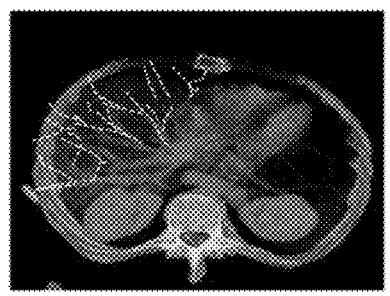

At first, the medical image diagnostic apparatus 100B extracts the structure of the subject (for example, the blood vessel of the subject here) included in the medical image data for image registration by the extraction circuitry 101 (step S1000). For example, a curve shown by a solid line in FIG. 11C is extracted from the ultrasonic image, and a curve shown by a dash line in FIG. 11D is extracted from the CT image.

Then, the medical image diagnostic apparatus 100B sets the display scale of the medical image to a specified value by the scale setting circuitry 102 (step S1002).

Then, the medical image diagnostic apparatus 100B performs pre-registration between the medical image data though the methods such as image matching and so on by the image registration circuitry 103 based on the blood vessel extracted by the extraction circuitry 101 (the point or line shown by a solid line in FIG. 11C and the line shown by a dash line in FIG. 11D) to generate a pre-registered image (step S1004).

Here, the pre-registered image is generated by superposing the ultrasound image (i.e., the curve shown by a solid line in FIG. 11C) and the CT image (i.e., the curve shown by a dash line in FIG. 11D) in a roughly overlapping way.

Then, the user can determine whether the pre-registered image is poorly pre-registered based on the displayed pre-registered image (step S1006). If the pre-registered image is determined as being poorly pre-registered (YES in step S1006), the user may input a correction instruction via the input circuitry 106 (step S1008), where the input correction instruction is rotation and translation, and the determination in step S1006 is performed again. If the determination result is that the pre-registered image is not poorly registered (No in step S1006), the process proceeds to step S1010.

Figure 11E:
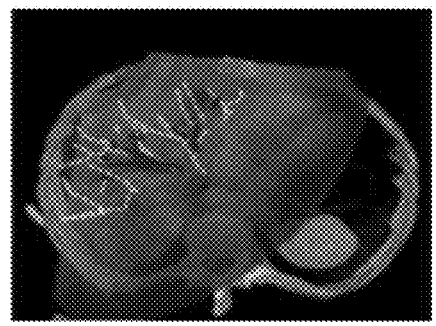
Figure 11F:
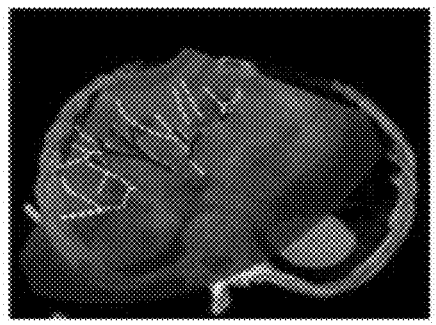
Figure 11G:
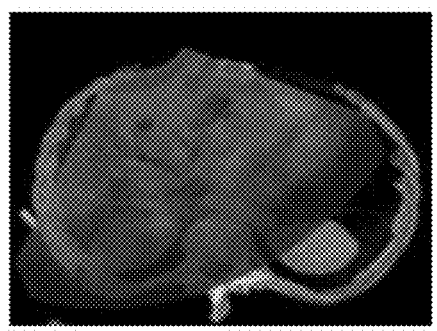

Then, the medical image diagnostic apparatus 100A performs formal image registration for the pre-registered image by the image registration circuitry 103 based on the structure extracted by the extraction circuitry 101 and the image information such as the grayscale and gradient and so on included in the image to generate registered image (step S1010), and then the operation process ends. Here, the registered image is generated by means of superposing the ultrasound image (i.e., the curve shown by a solid line in FIG. 11C) and the CT image (i.e., the curve shown by a dash line in FIG. 11D) in an overlapping way better than that in the pre-registered image shown in FIG. 11E, as shown in FIG. 11F. Further, the registered image may be displayed after the ultrasound image and the CT image are registered, but may not clearly represent the matching situation of the structure, as shown in FIG. 11G.

The medical image diagnostic apparatus 100B according to the third embodiment also has the technical effects of the first embodiment and the second embodiment. Further, since the medical image diagnostic apparatus 100B has the input circuitry 105 and the user can determine whether the pre-registered image is poorly registered after the image pre-registration is performed by the image registration circuitry 103, the user may adjust the image pre-registration manually to eliminate the poor pre-registration as much as possible if the pre-registration is poorly performed. As such, it is not necessary for the user to confirm the registration result after the time-consuming image registration is completed as in the prior art, and the user can confirm the pre-registration result and perform effective adjustment after the pre-registration which is not time-consuming, thereby enabling to further shorten the time required for image registration, realizing short image registration time and good real-time performance. Further, the user can easily and intuitively adjust the registration by rotating and/or translating one party of the image data or performing operation such as point designation and so on in both parties of the medical image data. In this way, the user can eliminate poor pre-registration as much as possible with less operation, thereby enabling reduced and easy user operation, providing an appropriate timing and manner of user interaction and improving the operational comfort of the medical image diagnostic apparatus.

(Modification)

Although the respective embodiments have been described above, the present invention is not limited to the above-described embodiments and modifications. For example, those skilled in the art can appropriately add and delete the structure elements, design modifications and appropriately combine the features in the respective embodiments or modifications for the respective embodiments described above, which are all included in the scope of the present invention, as long as they conforms the technical idea of the present invention.

For example, in the third embodiment, the scale adjustment may be performed during the process of the image calibration, for example, the scales of feature extraction and/or the image display may be adjusted.

Further, in step S714 of the second embodiment, the image registration circuitry 103 determines whether the objective function converges. Of course, it is possible to separately provide one determination circuitry to determine whether the objective function converges. Moreover, if there is control circuitry for controlling the overall operation of the medical image diagnostic apparatus 100B, it is also possible for the control circuitry to determine whether the objective function converges. The determination circuitry is realized by using a processor, for example. The control circuitry is realized by using a processor, for example.

Further, in the above embodiment, the case where the user inputs the correction instruction when the pre-calibration is poorly performed is described, but this is a preferable embodiment, and the embodiment is not limited thereto, and the process that the user inputs correction instruction may be performed in any stage of the image calibration process.

Further, in the above embodiment, the structure of the subject in the medical image data is extracted by the extraction circuitry at first, and then the display scale of the medical image is set by the scale setting circuitry. However, the present embodiment is not limited thereto, and it may also the situation that the display scale of the medical image is set by the scale setting circuitry at first, and then the structure of the subject in the medical image data is extracted by the extraction circuitry.

Further, in the respective embodiments described above, the image registration is described between the ultrasonic image and the CT image as an example. However, the above embodiment can of course be applied to the registration between the ultrasonic image and the MR image.

Further, the above image after the registration is displayed as a two-dimensional MPR image, but the embodiment is not limited thereto, and the above image after the registration may also be displayed by, for example, a three-dimensional SVR image.

Further, in the present embodiment, only the registered image may be displayed, or all or a part of the respective images related to the display example of the embodiment may be simultaneously displayed.

Further, the present embodiment describes in detail specific embodiments of the medical image diagnostic apparatus and the medical image diagnostic method performed thereby, but the specific embodiments is not limited thereto, and can also be implemented as the ultrasound diagnostic apparatus, integrated circuit, program and medium having the program recorded thereon etc. which including the medical image diagnostic apparatus.

The term "processor" used in the above description of the first and the second embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory.

According to at least one aspect of the embodiments described above, it is possible to achieve high registration accuracy, reduced user operation, easy user operation, short time consumption and good real-time performance.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus for performing image registration between two pieces of medical image data, comprising
processing circuitry configured to:
extract a structure of a subject included in the two pieces of medical image data;
set a pre-registration display scale of both of the two pieces of medical image data to a first specified value larger than current values of display scales to which the two pieces of medical image data are currently set,
perform pre-registration between the two pieces of medical image data based on the extracted structure on the pre-registration display scale of the first specified value to generate a pre-registered image,
set plural registration display scales for the pre-registered image to plural display scales of second specified values smaller than the first specified value, and
perform formal image registrations for the pre-registered image on the plural registration display scales having the second specified values based on the extracted structure and image information included in the two pieces of medical image data to generate a registered image; and
a display configured to display the registered image.

2. The medical image diagnostic apparatus according to claim 1, wherein the structure is a blood vessel or a surface contour.

3. The medical image diagnostic apparatus according to claim 1, wherein
the image information is a grayscale of the image.

4. The medical image diagnostic apparatus according to claim 1, further comprising:
an input interface which inputs a correction instruction by at least an operator,
wherein the input interface accepts the correction instruction input by the operator when the performed registration is poor.

5. The medical image diagnostic apparatus according to claim 4, wherein
the correction instruction from the input interface is at least one of rotation and translation of one party of the medical image data.

6. The medical image diagnostic apparatus according to claim 1, wherein the image information is a gradient of the image.

7. The medical image diagnostic apparatus according to claim 4, wherein the correction instruction from the input interface is point designation in both parties of the medical image data.

8. The medical image diagnostic apparatus according to claim 1, wherein processing circuitry configured to perform pre-registration comprises processing circuitry configured to perform vessel tree matching at the first specified value and using a first weight of a vessel tree distance to generate the pre-registered image.

9. The medical image diagnostic apparatus according to claim 8, wherein processing circuitry configured to perform the formal registrations comprises processing circuitry configured to perform vessel tree matching (a) at a display scale corresponding to one of the second specified values smaller than the first specified value and (b) using a second weight of the vessel tree distance smaller than the first weight of the vessel tree distance to generate the registered image.

10. The medical image diagnostic apparatus according to claim 1, wherein the two pieces of medical image data are two images of a same organ of the subject obtained using first and second imaging modalities that are different.

11. The medical image diagnostic apparatus according to claim 10, wherein the first imaging modality is ultrasound and the second imaging modality is computed tomography.

12. A medical image diagnosis method for performing image registration between two pieces of medical image data, comprising:

extracting a structure of a subject included in the two pieces of medical image data;

setting a pre-registration display scale of both of the two pieces of medical image data to a first specified value larger than current values of display scales to which the two pieces of medical image data are currently set, performing pre-registration between the two pieces of medical image data based on the extracted structure on the pre-registration display scale of the first specified value to generate a pre-registered image, setting plural registration display scales for the pre-registered image to plural display scales of second specified values smaller than the first specified value, and performing formal image registration for the pre-registered image on the plural registration display scales having the second specified values based on the extracted structure and image information included in the two pieces of medical image data to generate a registered image.

13. An ultrasonic diagnostic apparatus, comprising a medical image diagnostic apparatus comprising processing circuitry configured to:

extract a structure of a subject included in two pieces of medical image data;

set a pre-registration display scale of both of the two pieces of medical image data to a first specified value larger than current values of display scales to which the two pieces of medical image data are currently set, perform pre-registration between the two pieces of medical image data based on the extracted structure on the pre-registration display scale of the first specified value to generate a pre-registered image, and set plural registration display scales for the pre-registered image to plural display scales of second specified values smaller than the first specified value, and perform formal image registration for the pre-registered image on the plural registration display scales having the second specified values based on the extracted structure and image information included in the two pieces of medical image data to generate a registered image; and a display configured to display the registered image.

* * * * *